United States Patent
Matsushita et al.

(10) Patent No.: US 9,439,872 B2
(45) Date of Patent: Sep. 13, 2016

(54) ORAL FILM-FORM BASE AND PREPARATION

(71) Applicant: NITTO DENKO CORPORATION, Ibaraki-shi, Osaka (JP)

(72) Inventors: Kyohei Matsushita, Ibaraki (JP); Daisuke Asari, Ibaraki (JP); Takuya Shishido, Ibaraki (JP); Mitsuhiko Hori, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/813,797

(22) Filed: Jul. 30, 2015

(65) Prior Publication Data

US 2016/0058711 A1 Mar. 3, 2016

(30) Foreign Application Priority Data

Aug. 27, 2014 (JP) .................. 2014-173100

(51) Int. Cl.
  *A61F 13/02* (2006.01)
  *A61K 9/70* (2006.01)
  (Continued)

(52) U.S. Cl.
  CPC .............. *A61K 9/7007* (2013.01); *A23L 1/305* (2013.01); *A23L 1/3012* (2013.01); *A23L 1/3051* (2013.01); *A61K 9/00* (2013.01); *A61K 9/0056* (2013.01); *A61K 9/2054* (2013.01); *A61K 9/70* (2013.01); *A61K 9/7015* (2013.01); *A61K 31/137* (2013.01); *A61K 31/138* (2013.01); *A61K 31/18* (2013.01); *A61K 31/422* (2013.01); *A61K 31/426* (2013.01); *A61K 31/439* (2013.01); *A61K 31/46* (2013.01); *A61K 31/48* (2013.01); *A61K 31/7052* (2013.01);

(Continued)

(58) Field of Classification Search
  CPC ... A61K 9/0056; A23L 1/3012; A23L 1/305; A23L 1/3051
  See application file for complete search history.

(56) References Cited

U.S. PATENT DOCUMENTS 6,455,053 B1 9/2002 Okada et al.
2005/0147653 A1 7/2005 Yasuda et al.
(Continued)

FOREIGN PATENT DOCUMENTS

EP  1 522 225 A1  4/2005
EP  2 462 928 A1  6/2012
(Continued)

OTHER PUBLICATIONS

European Search Report dated Jan. 4, 2016, issued in counterpart EP Application No. 15002461.0.

*Primary Examiner* — Carlos Azpuru
(74) *Attorney, Agent, or Firm* — Sughrue Mion, PLLC (57) ABSTRACT

The present invention aims to provide an oral film-form base and an oral film-form preparation which have a rapid dissolution profile in the mouth and sufficient film strength, give a good tactile impression when handled with fingers and favorable texture and taste in the mouth, and are administrable to those who have limitation in carbohydrate intake. The present invention relates to an oral film-form base including an edible polymer soluble in water and an organic solvent having a solubility parameter of 9.7 or higher, and particles of at least one compound selected from the group consisting of amino acid, dipeptide, and nucleotide, the particles of at least one compound selected from the group consisting of amino acid, dipeptide, and nucleotide being dispersed in the state of particles in the oral film-form base.

9 Claims, 1 Drawing Sheet

(51) Int. Cl.
| | |
|---|---|
| *A23L 1/30* | (2006.01) |
| *A23L 1/305* | (2006.01) |
| *A61K 38/00* | (2006.01) |
| *A61K 9/00* | (2006.01) |
| *A61K 47/36* | (2006.01) |
| *A61K 9/20* | (2006.01) |
| *A61K 31/48* | (2006.01) |
| *A61K 31/7052* | (2006.01) |
| *A61K 31/715* | (2006.01) |
| *A61K 31/79* | (2006.01) |
| *A61K 31/137* | (2006.01) |
| *A61K 31/138* | (2006.01) |
| *A61K 31/18* | (2006.01) |
| *A61K 31/422* | (2006.01) |
| *A61K 31/426* | (2006.01) |
| *A61K 31/439* | (2006.01) |
| *A61K 31/46* | (2006.01) |
| *A61K 47/18* | (2006.01) |
| *A61K 47/32* | (2006.01) |
| *A61K 47/38* | (2006.01) |

(52) U.S. Cl.
CPC ............ *A61K 31/715* (2013.01); *A61K 31/79* (2013.01); *A61K 38/00* (2013.01); *A61K 47/183* (2013.01); *A61K 47/32* (2013.01); *A61K 47/36* (2013.01); *A61K 47/38* (2013.01)

(56) References Cited

U.S. PATENT DOCUMENTS

| | | |
|---|---|---|
| 2011/0293673 A1 | 12/2011 | Asari et al. |
| 2013/0177605 A1 | 7/2013 | Asari et al. |

FOREIGN PATENT DOCUMENTS

| | | |
|---|---|---|
| JP | 11-116465 A | 4/1999 |
| JP | 2004-43450 A | 2/2004 |
| JP | 3496727 B2 | 2/2004 |
| JP | 2007-528876 A | 10/2007 |
| JP | 2008-169138 A | 7/2008 |
| WO | 2004/045537 A2 | 6/2004 |
| WO | 2004/066986 A1 | 8/2004 |
| WO | 2005/082048 A2 | 9/2005 |
| WO | 2010/002418 A2 | 1/2010 |
| WO | 2010/087032 A1 | 8/2010 |
| WO | 2010/103539 A2 | 9/2010 |

ORAL FILM-FORM BASE AND PREPARATION

TECHNICAL FIELD

The present invention relates to a film-form base and a film-form preparation (pharmaceutical) that rapidly dissolve in the mouth. More specifically, the present invention relates to an orally administrative film-form base and an orally administrative film-form preparation that rapidly dissolve in the mouth so that a drug is absorbed through the gastrointestinal tract or oral mucosa.

BACKGROUND ART

Orally administrable film-, tape-, or sheet-form preparations that are to be disintegrated or dissolved by saliva without being chewed are already available as ten or more over-the-counter drugs (OTC drugs) overseas. In Japan, those preparations are available as several ethical pharmaceuticals.

Such a film-form preparation contains a drug dispersed or dissolved in a film-form base. In an exemplary method of producing thereof, a water-soluble polymer is dissolved in a solvent and a drug is dissolved or dispersed therein, and the resulting dispersion or solution is formed into a film and then dried.

The following patent literatures disclose such film-form preparations. Patent Literature 1 discloses a preparation including a film-form base formed of a tannin substance and hydroxypropyl cellulose or a mixture of hydroxypropyl cellulose and polyvinyl pyrrolidone, and a drug added to the film-form base. Patent Literature 2 discloses a film-form preparation containing a drug, an edible water-soluble film forming agent, and low-substituted hydroxypropyl cellulose. Patent Literature 3 discloses a rapidly dissolving film-form preparation that contains a drug and an edible polymer substance, has a breaking strength and a tensile strength within predetermined ranges, and dissolves within 60 seconds in the mouth. Patent Literature 4 discloses a soluble film that contains an active ingredient having a water solubility of less than about 1 g/4 mL at room temperature and has a water content of less than about 15% by weight. Though it is not in the film form, Patent Literature 5 discloses a rapidly dissolving preparation that is obtainable by dissolving/dispersing a drug, a saccharide, and polyvinyl pyrrolidone in an organic solvent to prepare a suspension, filling the suspension in a mold for preparations, and removing the organic solvent.

However, many of the film-form preparations having been disclosed up to now contain sugar or sugar alcohol as an excipient for ensuring the film strength. The sugar or sugar alcohol is in the state of being dissolved or recrystallized in the solvent. For this reason, those conventional film-form preparations give a sticky feeling attributed to the water-soluble polymer in the mouth. Moreover, the sticky feeling when handled with the fingers is also a problem.

To solve such problems, Patent Literature 6 discloses a method of improving the disintegration property of an oral film-form base and an oral film-form preparation in the mouth while preventing dissolution or recrystallization of sugar or sugar alcohol by dispersing particles of the sugar or sugar alcohol in the film containing an edible polymer. Further, various studies are also made on the size of particles added to film-form preparations (see Patent Literatures 7 to 9).

CITATION LIST

Patent Literature

Patent Literature 1: Japanese Patent No. 3496727
Patent Literature 2: JP-A 2008-169138
Patent Literature 3: JP-A 2004-43450
Patent Literature 4: JP-T 2007-528876
Patent Literature 5: JP-A H11-116465
Patent Literature 6: WO 2010/087032
Patent Literature 7: WO 2004/066986
Patent Literature 8: WO 2004/045537
Patent Literature 9: WO 2010/103539

SUMMARY OF INVENTION

Technical Problem

When sugar or sugar alcohol is used as an excipient, however, the sticky feeling attendant on moisture absorption by a saccharide adversely affects the tactile impression. For another problem, administration of such preparations to those who have limitation in carbohydrate intake (e.g., those who need blood sugar level control) has to be avoided. Moreover, though various studies have been made on the size of particles added to film-form preparations (see, for example, Patent Literatures 7 to 9), the method of controlling the particle size or the particle form has not been sufficiently studied.

In consideration of the state of the art, the present invention aims to provide an oral film-form base and an oral film-form preparation which have a rapid dissolution profile in the mouth and sufficient film strength, give a good tactile impression when handled with fingers and favorable texture and taste in the mouth, and are administrable to those who have limitation in carbohydrate intake.

Solution to Problem

The present inventors have made various studies to solve the above problems, and have found that an oral film-form base and an oral film-form preparation, if the film-form base contains the following constituents, have a rapid dissolution profile in the mouth and sufficient film strength, gives a good tactile impression when handled with fingers and favorable texture and taste in the mouth, and are administrable to those who have limitation in carbohydrate intake. Specifically, the film-form base includes an edible polymer soluble in water and an organic solvent having a solubility parameter of 9.7 or higher and at least one compound selected from the group consisting of amino acid, dipeptide, and nucleotide dispersed in the state of particles. The present invention has been thus completed.

The present invention relates to an oral film-form base including an edible polymer soluble in water and an organic solvent having a solubility parameter of 9.7 or higher, and particles of at least one compound selected from the group consisting of amino acid, dipeptide, and nucleotide, the particles of at least one compound selected from the group consisting of amino acid, dipeptide, and nucleotide being dispersed in the state of particles in the oral film-form base.

The particles of at least one compound selected from the group consisting of amino acid, dipeptide, and nucleotide preferably have an average particle size of 0.1 to 60 µm.

The edible polymer soluble in water and an organic solvent having a solubility parameter of 9.7 or higher is preferably solid at ambient temperature.

The edible polymer soluble in water and an organic solvent having a solubility parameter of 9.7 or higher is preferably at least one of polyvinyl pyrrolidone and hydroxypropyl cellulose.

The polyvinyl pyrrolidone preferably has a weight average molecular weight of 2500 to 3000000.

The hydroxypropyl cellulose preferably has a weight average molecular weight of 10000 to 1150000.

The hydroxypropyl cellulose preferably has a hydroxypropoxyl substitution degree of 50 to 100%.

The oral film-form base of the present invention is preferably produced using an organic solvent having a solubility parameter of 9.7 or higher.

The present invention also relates to an oral film-form preparation including the oral film-form base of the present invention, and a drug dispersed or dissolved in the oral film form base.

The present invention is specifically described in the following.

The oral film-form base of the present invention contains an edible polymer soluble in water and an organic solvent having a solubility parameter of 9.7 or higher, and particles of at least one compound selected from the group consisting of amino acid, dipeptide, and nucleotide. The particles of at least one compound selected from the group consisting of amino acid, dipeptide, and nucleotide are dispersed in the oral film-form base of the present invention in the state of particles.

The oral film-form base of the present invention having such a structure has a rapid dissolution profile in the mouth and sufficient film strength, and gives a good tactile impression when handled with fingers and favorable texture and taste in the mouth. Moreover, in comparison with those containing sugar or sugar alcohol, the oral film-form base of the present invention containing particles of at least one compound selected from the group consisting of amino acid, dipeptide, and nucleotide prevents worsening of the tactile impression (giving sticky feeling) attendant on moisture absorption by a saccharide and is administrable to those who have limitation in carbohydrate intake.

The phrase "dispersed in the state of particles" as used herein refers to a state where particles are not dissolved or recrystallized but dispersed while maintaining the state of particles. A person skilled in the art would easily and clearly distinguish amino acid and the like contained in the recrystallized state in the oral film-form base from amino acid and the like contained in the state of particles in the oral film-form base by microscopic observation or the like.

In other words, amino acid and the like in the oral film-form base are spontaneously recrystallized and contained in the recrystallized state, and therefore have irregular and inhomogeneous shapes and sizes which are sometimes described as an amorphous state. In the case of the amino acid and the like dispersed in the state of particles in the oral film-form base, the manufacturer controls the particle size in production of the film-form base, so that the amino acid and the like have artificial shapes and sizes.

Figure 1:
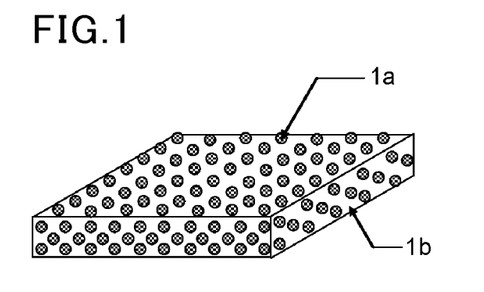
FIG. 1 is a schematic view illustrating an exemplary embodiment of the oral film-form base of the present invention.

FIG. 1 is a schematic view illustrating an exemplary embodiment of the oral film-form base of the present invention. As illustrated in FIG. 1, in the oral film-form base of the present invention, particles 1a of at least one compound selected from the group consisting of amino acid, dipeptide, and nucleotide are dispersed in the state of particles in an edible film 1b made of an edible polymer.

The particles of at least one compound selected from the group consisting of amino acid, dipeptide, and nucleotide are added as an excipient for the purpose of ensuring the film strength.

The particles of at least one compound selected from the group consisting of amino acid, dipeptide, and nucleotide are preferably insoluble in an organic solvent having a solubility parameter of 9.7 or higher.

At least one compound selected from the group consisting of amino acid, dipeptide, and nucleotide can be dispersed in the state of particles, and the particle size and the particle form can be controlled, provided that the particles of at least one compound selected from the group consisting of amino acid, dipeptide, and nucleotide used have the above dissolution property, that a later-described edible polymer soluble in water and an organic solvent having a solubility parameter of 9.7 or higher is used, and that an organic solvent having a solubility parameter of 9.7 or higher is used as a solvent in the production.

The term "solubility parameter" (also referred to as SP value) as used herein refers to the square root $((cal/cm^3)^{1/2})$ of the heat of evaporation $(cal/cm^3)$ required for evaporating one molar volume of a liquid. When a substance is said to be "insoluble" in a solvent, the amount of the solvent needed for dissolving 1 g of the substance (solute) at 20° C. is 100 mL or more. When a substance is said to be "soluble" in a solvent, the amount of the solvent needed for dissolving 1 g of the substance (solute) at 20° C. is less than 5 mL. If a substance is said to be "easily soluble" in a solvent, the amount of the solvent needed for dissolving 1 g of the substance (solute) at 20° C. is less than 3 mL.

For easy formation of particles, the particles of at least one compound selected from the group consisting of amino acid, dipeptide, and nucleotide are preferably solid at ambient temperature.

The phrase "solid at ambient temperature" as used herein refers to the absence of fluidity at 20° C.

The particles of at least one compound selected from the group consisting of amino acid, dipeptide, and nucleotide are preferably dispersed in the state of particles of itself in the oral film-form base of the present invention, without coating, for example, by microencapsulation or the like. Such particles without coating take effect immediately after administration, and production thereof does not require a complicated procedure.

The particles of at least one compound selected from the group consisting of amino acid, dipeptide, and nucleotide may have any particle size, as long as they are in the particle form. Preferably, the average particle size thereof is 0.1 to 60 μm. If the particle size is less than 0.1 μm, the particles may be aggregated. In such a case, the flexibility of the oral film-form base may vary from part to part. If the particle size is more than 60 μm, when the oral film-form base having a reasonable thickness contains such particles, the flexibility thereof may vary from part to part. The average particle size is more preferably 0.5 to 40 μm.

The average particle size of the particles of at least one compound selected from the group consisting of amino acid, dipeptide, and nucleotide as used herein refers to the 50% by volume average particle size measured with a laser scattering particle size distribution analyzer.

If the particles of at least one compound selected from the group consisting of amino acid, dipeptide, and nucleotide have an average particle size outside the range mentioned above, the particles may be subjected to sizing so as to have an average particle size within the above range. The average particle size can be adjusted by granulation such as grinding, dry grinding, or wet granulation, or by classification using a sieve or a classifying apparatus.

The amino acid is not particularly limited, and preferred examples thereof include glycine, alanine, valine, leucine, isoleucine, proline, serine, threonine, cysteine, methionine, aspartic acid, glutamic acid, asparagine, glutamine, lysine, arginine, histidine, phenylalanine, tyrosine, tryptophan, hydroxyproline, and pharmaceutically acceptable salts of these. Each of these amino acids may be used alone, or two or more of these may be used in combination.

The dipeptide is not particularly limited as long as it is a molecule including two amino acids bonded by a peptide bond. Preferred examples thereof include molecules including the same kind or different kinds of amino acids, which are selected from the above-mentioned amino acids, bonded by peptide bonds and pharmaceutically acceptable salts thereof. Each of these dipeptides may be used alone, or two or more of these may be used in combination.

The nucleotide is not particularly limited, and preferred examples thereof include adenylic acid, thymidylic acid, guanylic acid, cytidylic acid, inosinic acid, and pharmaceutically acceptable salts thereof. Each of these nucleotides may be used alone, or two or more of these may be used in combination.

The amount of the particles of at least one compound selected from the group consisting of amino acid, dipeptide, and nucleotide is preferably 5 to 80% by weight in the total weight of the solid content of the oral film-form base or oral film-form preparation of the present invention. If the amount is less than 5% by weight, the rapid dissolution profile in the mouth or sufficient film strength may not be achieved. In contrast, if the amount is more than 80% by weight, the shape retention of the product may be disadvantageously lowered unless the particle size of the particles of at least one compound selected from the group consisting of amino acid, dipeptide, and nucleotide is significantly reduced. The amount is more preferably 10 to 60% by weight.

The edible polymer soluble in water and an organic solvent having a solubility parameter of 9.7 or higher is not particularly limited, as long as it is edible and soluble in water and an organic solvent having a solubility parameter of 9.7 or higher and has a relatively large molecular weight to have a film-forming ability. Preferably, the edible polymer is solid at ambient temperature.

Such an edible polymer has a weight average molecular weight of preferably 2000 to 4000000. If the weight average molecular weight is less than 2000, the film-forming ability may be poor so that the shape of the oral film-form base may be hardly maintained. If the weight average molecular weight is more than 4000000, the solubility of the oral film-form base may be poor, leading to a problem in practical use. The weight average molecular weight is more preferably 2500 to 3000000.

Specifically, the edible polymer soluble in water and an organic solvent having a solubility parameter of 9.7 or higher is preferably polyvinyl pyrrolidone (hereafter, abbreviated to "PVP") and/or hydroxypropyl cellulose (hereafter, abbreviated to "HPC").

These edible polymers show sufficient solubility in water and an organic solvent having a solubility parameter of 9.7 or higher, and satisfy both of the following conditions that it is dissolved rapidly in the mouth and that the use thereof enables the use of a solvent in which particles of at least one compound selected from the group consisting of amino acid, dipeptide, and nucleotide are insoluble in production of the oral film-form base. The use thereof, therefore, allows at least one compound selected from the group consisting of amino acid, dipeptide, and nucleotide to be uniformly dispersed or supported in the state of particles.

More preferred among the edible polymers soluble in water and an organic solvent having a solubility parameter of 9.7 or higher is HPC. The reason for this is that HPC having lower hygroscopicity to relative humidity than PVP is preferred in terms of the practical use. Each of these edible polymers soluble in water and an organic solvent having a solubility parameter of 9.7 or higher may be used alone, or two or more of these may be used in combination.

The PVP has a weight average molecular weight of preferably 2500 to 3000000. If the weight average molecular weight is less than 2500, the stability and hygroscopicity may be lowered. If the weight average molecular weight is more than 3000000, the solubility may be lowered. The weight average molecular weight is more preferably 2500 to 1200000.

The HPC has a weight average molecular weight of preferably 10000 to 1150000. If the weight average molecular weight is less than 10000, the hygroscopicity and stability may be lowered. If the weight average molecular weight is more than 1150000, the solubility may be lowered. The weight average molecular weight is more preferably 10000 to 370000.

The molecular weight as used herein means the weight average molecular weight. The weight average molecular weight is determined by gel permeation chromatography.

The HPC has a hydroxypropoxyl substitution degree of preferably 50 to 100%. If the hydroxypropoxyl substitution degree is less than 50%, the solubility in an organic solvent may be lowered. The hydroxypropoxyl substitution degree is more preferably 53.4% or more.

The hydroxypropoxyl substitution degree is determined in conformity with Japanese Pharmacopoeia, fifteenth edition, Official monographs, Hydroxypropyl cellulose, Assay.

The oral film-form base of the present invention may contain an appropriate amount of other edible polymers in addition to the edible polymer soluble in water and an organic solvent having a solubility parameter of 9.7 or higher.

Examples of the other edible polymers include edible polymers soluble only in water and edible polymers insoluble in water and an organic solvent having a solubility parameter of 9.7 or higher. Specific examples thereof include synthetic polymers such as polyvinyl alcohol, carboxyvinyl polymer, hydroxypropyl methylcellulose (hereafter, abbreviated to "HPMC"), hydroxyethylcellulose, methylcellulose, ethyl cellulose, low-substituted hydroxypropyl cellulose, crystalline cellulose, carboxymethylcellulose sodium, carboxymethylcellulose calcium, carboxymethylcellulose, and carboxymethyl starch sodium; and polymers obtainable from natural products such as sodium alginate, dextran, casein, pullulan, pectin, guar gum, xanthan gum, tragacanth gum, acacia gum, Arabian gum, and starch.

The total amount of the edible polymer soluble in water and an organic solvent having a solubility parameter of 9.7 or higher and the other edible polymers is preferably 1 to 80% by weight of the total weight of the solid content of the oral film-form base or preparation of the present invention. If the total amount is less than 1% by weight, the amount of the particles of at least one compound selected from the group consisting of amino acid, dipeptide, and nucleotide may be too large. In such a case, the shape retention of the product may be disadvantageously lowered unless the particle size of the particles of at least one compound selected from the group consisting of amino acid, dipeptide, and nucleotide is significantly reduced. If the total amount is more than 80% by weight, the rapid dissolution profile in the mouth or sufficient film strength may not be achieved. The total amount is more preferably 10 to 70% by weight.

The oral film-form base of the present invention may optionally contain, in addition to the above substances, flavors, taste-masking agents, sweeteners, colorants, preservatives, anti-oxidants, stabilizers, surfactants, plasticizers (e.g., polyethylene glycol (PEG)) as appropriate. Since the oral film-form base of the present invention contains the particles of at least one compound selected from the group consisting of amino acid, dipeptide, and nucleotide as an excipient, the oral film-form base preferably does not contain sugar or sugar alcohol that is conventionally used as an excipient. The oral film-form base of the present invention, however, may contain sugar or sugar alcohol as long as it does not impair the effect of the present invention.

The oral film-form preparation of the present invention includes the oral film-form base of the present invention and a drug dispersed or dissolved in the oral film-form base.

The drug may be dispersed or dissolved in the oral film-form base of the present invention. When the drug is dispersed, the drug is preferably insoluble in an organic solvent having a solubility parameter of 9.7 or higher. For easy formation of drug particles, the drug is more preferably solid at ambient temperature.

The drug is not particularly limited as long as it is orally administrable. Examples thereof include sedatives, expectorants, laxatives, anti-cancer drugs, anti-diabetic drugs, anti-parkinsonian drugs, antidepressants, tranquilizers, dementia drugs, hypotensive drugs, hyperlipemia drugs, migraine drugs, drugs for treatment of osteoporosis, drugs for treatment of hypotension, antitussives, peptic ulcer drugs, pollakisuria/dysuria drugs, urinary incontinence drugs, anti-ulcer drugs, antiallergic drugs, and 5-HT3 receptor antagonists (antiemetic drugs). The drug is preferably not bitter. However, even a bitter drug can be suitably used with an aid of bitterness masking techniques (e.g., microencapsulation, addition of bitterness masking agents, sweeteners, flavoring agents or aromatic agents).

The amount of the drug depends on the characteristics thereof and is preferably 0.1 to 60% by weight in the total weight of the solid content of the oral film-form preparation of the present invention. If the amount is more than 60% by weight, the shape retention of the product may be disadvantageously lowered unless the particle size of the drug is significantly reduced.

The thickness of the oral film-form base and the oral film-form preparation of the present invention is not particularly limited, and is preferably 30 to 300 μm. If the thickness is less than 30 μm, the film strength and handleability of the product may be disadvantageously lowered. If the thickness is more than 300 μm, dissolution in the mouth takes time, so that the oral film-form base and the oral film-form preparation may not be easily dissolved.

The planar shapes of the oral film-form base and the oral film-form preparation of the present invention are not particularly limited, and may be any shapes such as rectangular, square, and circular shapes.

The oral film-form base and the oral film-form preparation of the present invention can be produced by, for example, the following method.

First, a predetermined amount of an edible polymer is dissolved in a solvent (e.g., ethanol, propanol, acetone). To the resulting solution, a drug is dispersed or dissolved in the case of producing a preparation, and a predetermined amount of particles of at least one compound selected from the group consisting of amino acid, dipeptide, and nucleotide are homogeneously dispersed to give a dispersion. Here, the particles are preliminary subjected to grinding, granulation, or treatment with a classifier so that the particle size thereof is adjusted. A proper amount of the resulting dispersion is spread on a release film and dried to provide a film. The oral film-form base and the oral film-form preparation are thus produced. Moreover, the dried oral film-form base and the oral film-form preparation are each cut to a desired size and optionally sealed hermetically as a product.

If bubbles are formed during the preparation of the dispersion, the dispersion is preferably left over night or subjected to vacuum deaeration.

The solvent used in production of the oral film-form base and the oral film-form preparation of the present invention is not particularly limited, as long as particles of at least one compound selected from the group consisting of amino acid, dipeptide, and nucleotide are not dissolved therein but an edible polymer soluble in water and an organic solvent having a solubility parameter of 9.7 or higher is dissolved therein. Preferably, an organic solvent having a solubility parameter of 9.7 or higher is used.

In other words, the oral film-form base and the oral film-form preparation of the present invention are preferably produced using an organic solvent having a solubility parameter of 9.7 or higher.

The organic solvent having a solubility parameter of 9.7 or higher preferably has a solubility parameter of 9.7 to 20 and more preferably 9.7 to 15. If the solubility parameter is higher than 20, the particles of at least one compound selected from the group consisting of amino acid, dipeptide, and nucleotide may be unintendedly dissolved in the solvent depending on the kind of the particles.

Specifically, as the organic solvent having a solubility parameter of 9.7 or higher, preferred are ethanol, propanol, and acetone. More preferred is ethanol. Each of these organic solvents having a solubility parameter of 9.7 or higher may be used alone, or two or more of these may be used in combination. To these organic solvents having a solubility parameter of 9.7 or higher, a slight amount of water (purified water) may be added.

Table 1 shows the solubility parameters (SP values) of water and the organic solvents having a solubility parameter of 9.7 or higher.

TABLE 1

| Solvent | Solubility parameter (SP value) |
|---|---|
| Methanol | 14.5-14.8 |
| Ethanol | 12.7 |
| Isopropanol | 11.5 |
| Propylene glycol | 14.3 |
| Methylene chloride | 9.7 |
| Acetone | 10 |
| Water | 23.4 |

Advantageous Effects of Invention

The oral film-form base and the oral film-form preparation of the present invention have a rapid dissolution profile in the mouth and sufficient film strength, and give a good tactile impression when handled with fingers and favorable texture and taste in the mouth. In comparison with those containing sugar or sugar alcohol, the oral film-form base and the oral film-form preparation of the present invention, which contain particles of at least one compound selected from the group consisting of amino acid, dipeptide, and nucleotide, prevent worsening of the tactile impression (giving sticky feeling) attendant on moisture absorption and are administrable to those who have limitation in carbohydrate intake.

In production of the oral film-form base and the oral film-form preparation of the present invention, the particles of at least one compound selected from the group consisting of amino acid, dipeptide, and nucleotide do not need to be preliminary dissolved in the solution but can be dispersed or supported in the state of particles. Accordingly, the oral film-form base and the oral film-form preparation of the present invention can be efficiently produced, and the particle size and the particle form can be controlled.

DESCRIPTION OF EMBODIMENTS

The present invention is specifically described with reference to, but not limited to, examples in the following.

Particles of amino acid, dipeptide, or nucleotide used in examples and comparative examples were preliminary ground and passed through a sieve having an aperture of 32 μm, 50 μm, or 90 μm. The 50% by volume average particle size of these particles was measured with a laser scattering particle size distribution analyzer, and the obtained particle size was used as the average particle size. Table 2 shows the 50% by volume particle size of the particles of amino acid, dipeptide, or nucleotide used in examples and comparative examples.

TABLE 2

| Amino acid, dipeptide, or nucleotide particles | 50% by volume average particle size [μm] |
| --- | --- |
| Sodium L-glutamate particles | 15 |
| Sodium L-aspartate particles | 12 |
| L-Alanine particles | 15 |
| Glycine particles | 14 |
| L-Lysine hydrochloride particles | 13 |
| L-Glutamine/L-lysine particles | 20 |
| L-Glutamic acid/L-arginine particles | 21 |
| Disodium inosinate particles | 16 |
| Disodium guanylate particles | 13 |

Examples 1 and 2

To 60.0 parts by weight of ethanol (solubility parameter of 12.7) were added 40.0 parts by weight of HPC (soluble in water and an organic solvent having a solubility parameter of 9.7 or higher, molecular weight of about 30000, hydroxypropoxyl substitution degree of 53.4 to 77.5%) or PVP (soluble in water and an organic solvent having a solubility parameter of 9.7 or higher, molecular weight of 1050000 to 1200000, PVP K-30) and dissolved with stirring to give an ethanol solution of HPC or PVP.

Separately, to an appropriate amount of ethanol was added 9.0 parts by weight of zolmitriptan and dissolved with stirring. To the resulting solution were added 40.0 parts by weight of sodium L-glutamate particles preliminary passed through a sieve (aperture of 32 μm) and stirred with ultrasonic. To the resulting solution were added 117.5 parts by weight of the ethanol solution of HPC or PVP and 4.0 parts by weight of polyethylene glycol (PEG400) and mixed with stirring. The resulting liquid was sufficiently deaerated to give a dispersion.

The dispersion was spread on a polyester release film and dried to form a film having a thickness of about 100 μm. The obtained film was cut to a rectangle (size of 3 cm$^2$), thereby preparing an oral film-form preparation in which sodium L-glutamate particles were dispersed.

Comparative Examples 1, 2

An amount of 9.0 parts by weight of zolmitriptan was added to a small amount of ethanol and dissolved therein with heat. To 47.0 parts by weight of pullulan (soluble only in water) or HPMC (soluble only in water) were added 183.3 parts by weight or 200.0 parts by weight of purified water, 4.0 parts by weight of polyethylene glycol (PEG400), and 40.0 parts by weight of sodium L-glutamate particles preliminary passed through a sieve (aperture of 32 μm) and dissolved with stirring. To the resulting solution, the ethanol solution of zolmitriptan prepared in advance was added and dissolved therein with stirring while being heated at 45° C. The resulting liquid was sufficiently deaerated to give a solution.

The solution was spread on a polyester release film and dried to form a film having a thickness of about 100 μm. The obtained film was cut to a rectangle (size of 3 cm$^2$), thereby preparing an oral film-form preparation in which sodium L-glutamate was dissolved.

TABLE 3

| | Example [parts by weight] | | Comparative Example [parts by weight] | |
| --- | --- | --- | --- | --- |
| Component | 1 | 2 | 1 | 2 |
| Zolmitriptan | 9.0 | 9.0 | 9.0 | 9.0 |
| HPC | 47.0 | — | — | — |
| PVP K-30 | — | 47.0 | — | — |
| Pullulan | — | — | 47.0 | — |
| HPMC | — | — | — | 47.0 |
| PEG400 | 4.0 | 4.0 | 4.0 | 4.0 |
| Sodium L-glutamate particles | 40.0 | 40.0 | 40.0 | 40.0 |
| Purified water | — | — | 183.3 | 200.0 |
| Ethanol | 120.5 | 137.2 | 33.3 | 33.3 |

Examples 3 to 10

Oral film-form preparations containing particles of amino acid, dipeptide, or nucleotide dispersed therein were prepared in the same manner as in Example 1, except that the kind of the particles of amino acid, dipeptide, or nucleotide was changed and the formulation was changed as shown in Table 4.

TABLE 4

| Component | Example [parts by weight] | | | | | | | |
|---|---|---|---|---|---|---|---|---|
| | 3 | 4 | 5 | 6 | 7 | 8 | 9 | 10 |
| Zolmitriptan | 9.0 | 9.0 | 9.0 | 9.0 | 9.0 | 9.0 | 9.0 | 9.0 |
| HPC | 47.0 | 47.0 | 47.0 | 47.0 | 47.0 | 47.0 | 47.0 | 47.0 |
| PEG400 | 4.0 | 4.0 | 4.0 | 4.0 | 4.0 | 4.0 | 4.0 | 4.0 |
| Sodium L-aspartate particles | 40.0 | — | — | — | — | — | — | — |
| L-Alanine particles | — | 40.0 | — | — | — | — | — | — |
| Glycine particles | — | — | 40.0 | — | — | — | — | — |
| L-Lysine hydrochloride particles | — | — | — | 40.0 | — | — | — | — |
| L-Glutamine/L-lysine particles | — | — | — | — | 40.0 | — | — | — |
| L-Glutamic acid/L-arginine particles | — | — | — | — | — | 40.0 | — | — |
| Disodium inosinate particles | — | — | — | — | — | — | 40.0 | — |
| Disodium guanylate particles | — | — | — | — | — | — | — | 40.0 |
| Ethanol | 137.2 | 137.2 | 137.2 | 120.5 | 137.2 | 103.8 | 153.8 | 103.8 |

Examples 11 to 16

Oral film-form preparations containing sodium L-glutamate particles dispersed therein were prepared in the same manner as in Example 1, except that the kind of the drug was changed and the formulation was changed as shown in Table 5.

TABLE 5

| Component | Example [parts by weight] | | | | | |
|---|---|---|---|---|---|---|
| | 11 | 12 | 13 | 14 | 15 | 16 |
| Diphenhydramine hydrochloride | 50.0 | — | — | — | — | — |
| Tamsulosin hydrochloride | — | 0.7 | — | — | — | — |
| Granisetron hydrochloride | — | — | 10.0 | — | — | — |
| Tolterodine tartrate | — | — | — | 13.3 | — | — |
| Scopolamine hydrobromide | — | — | — | — | 0.8 | — |
| Famotidine | — | — | — | — | — | 25.0 |
| HPC | 36.0 | 40.3 | 36.0 | 37.7 | 40.2 | 36.0 |
| PEG400 | 4.0 | 4.0 | 4.0 | 4.0 | 4.0 | 4.0 |
| Sodium L-glutamate particles | 10.0 | 55.0 | 50.0 | 45.0 | 55.0 | 35.0 |
| Ethanol | 140.0 | 184.1 | 173.3 | 152.6 | 180.5 | 160.0 |

Comparative Example 3

An oral film-form preparation not containing any of amino acid, dipeptide, and nucleotide was prepared in the same manner as in Example 1, except that sodium L-glutamate particles were not used and the formulation was changed as shown in Table 6.

Comparative Examples 4 to 13

To 65.0 parts by weight of purified water was added 35.0 parts by weight of HPC (soluble in water and an organic solvent having a solubility parameter of 9.7 or higher, molecular weight of about 30000, hydroxypropoxyl substitution degree of 53.4 to 77.5%) and dissolved with stirring. Thus a solution of HPC in purified water was prepared.

Separately, to a trace amount of ethanol was added 9.0 parts by weight of zolmitriptan and dissolved with stirring. To the resulting solution was added 40.0 parts by weight of particles of amino acid, dipeptide, or nucleotide preliminary passed through a sieve (aperture of 32 μm) and stirred with ultrasonic. To the resulting solution were added 134.3 parts by weight of the solution of HPC in purified water and 4.0 parts by weight of polyethylene glycol (PEG400) and mixed with stirring. The resulting liquid was sufficiently deaerated to give a solution.

The solution was spread on a polyester release film and dried to form a film having a thickness of about 100 μm. The obtained film was tried to be removed from the polyester release film to prepare an oral film-form preparation. In Comparative Examples 4, 6, and 8 to 13, however, the oral film-form preparations were fragile and too soft, so that usable oral film-form preparations could not be obtained. In Comparative Examples 5 and 7, the obtained films having a thickness of about 100 μm were each cut to a rectangle (size of 3 $cm^2$), thereby preparing oral film-form preparations containing amino acid, dipeptide, or nucleotide dissolved therein.

TABLE 6

| Component | Comparative Example [parts by weight] | | | | | | | | | | |
|---|---|---|---|---|---|---|---|---|---|---|---|
| | 3 | 4 | 5 | 6 | 7 | 8 | 9 | 10 | 11 | 12 | 13 |
| Zolmitriptan | 9.0 | 9.0 | 9.0 | 9.0 | 9.0 | 9.0 | 9.0 | 9.0 | 9.0 | 9.0 | 9.0 |
| HPC | 87.0 | 47.0 | 47.0 | 47.0 | 47.0 | 47.0 | 47.0 | 47.0 | 47.0 | 47.0 | 87.0 |
| PEG400 | 4.0 | 4.0 | 4.0 | 4.0 | 4.0 | 4.0 | 4.0 | 4.0 | 4.0 | 4.0 | 4.0 |
| Sodium L-glutamate particles | — | 40.0 | — | — | — | — | — | — | — | — | — |
| Sodium L-aspartate particles | — | — | 40.0 | — | — | — | — | — | — | — | — |
| L-Alanine particles | — | — | — | 40.0 | — | — | — | — | — | — | — |
| Glycine particles | — | — | — | — | 40.0 | — | — | — | — | — | — |
| L-Lysine hydrochloride particles | — | — | — | — | — | 40.0 | — | — | — | — | — |
| L-Glutamine/L-lysine particles | — | — | — | — | — | — | 40.0 | — | — | — | — |
| L-Glutamic acid/L-arginine particles | — | — | — | — | — | — | — | 40.0 | — | — | — |
| Disodium inosinate particles | — | — | — | — | — | — | — | — | 40.0 | — | — |
| Disodium guanylate particles | — | — | — | — | — | — | — | — | — | 40.0 | — |
| Ethanol | 116.7 | 33.3 | 33.3 | 33.3 | 33.3 | 33.3 | 33.3 | 33.3 | 33.3 | 33.3 | 33.3 |
| Purified water | — | 170.6 | 170.6 | 137.3 | 137.3 | 137.3 | 137.3 | 137.3 | 137.3 | 137.3 | 137.3 |

Comparative Examples 14 to 22

Oral film-form preparations containing particles of sugar or sugar alcohol dispersed therein were prepared in the same manner as in Example 1, except that particles of sugar or sugar alcohol were used instead of sodium L-glutamate particles and the formulations were changed as shown in Table 7.

Here, the 50% by volume average particle size of the particles of sugar or sugar alcohol was measured with a laser scattering particle size distribution analyzer. D-Mannitol particles A had a 50% by volume average particle size of 17 μm. D-Mannitol particles B had a 50% by volume average particle size of 15 μm. D-Mannitol particles C had a 50% by volume average particle size of 16 μm. D-Mannitol particles D had a 50% by volume average particle size of 14 μm. Maltose particles had a 50% by volume average particle size of 20 μm. Glucose particles had a 50% by volume average particle size of 19 μm.

TABLE 7

| Component | Comparative Example [parts by weight] | | | | | | | | |
|---|---|---|---|---|---|---|---|---|---|
| | 14 | 15 | 16 | 17 | 18 | 19 | 20 | 21 | 22 |
| Zolmitriptan | 9.0 | 9.0 | 9.0 | — | — | — | — | — | — |
| HPC | 47.0 | 47.0 | 47.0 | 46.0 | 46.0 | 46.0 | 91.0 | 71.0 | 21.0 |
| PEG400 | 4.0 | 4.0 | 4.0 | 4.0 | 4.0 | 4.0 | 4.0 | 4.0 | 4.0 |
| D-Mannitol particles A | 40.0 | — | — | — | — | — | — | — | — |
| D-Mannitol particles B | — | — | — | 50.0 | — | — | 5.0 | 25.0 | 75.0 |
| D-Mannitol particles C | — | — | — | — | 50.0 | — | — | — | — |
| D-Mannitol particles D | — | — | — | — | — | 50.0 | — | — | — |
| Maltose particles | — | 40.0 | — | — | — | — | — | — | — |
| Glucose particles | — | — | 40.0 | — | — | — | — | — | — |
| Ethanol | 137.2 | 137.2 | 137.2 | 120.0 | 120.0 | 120.0 | 121.0 | 137.0 | 98.4 |

[Testing Method]

The following methods were employed for evaluating the releasability in production, dissolution profile in the mouth, film strength, tactile impression when handled with fingers, textures in the mouth, taste, and usability under limitation in carbohydrate intake of the oral film-form preparations of the examples and comparative examples.

(1) Releasability Test

The releasability of each oral film-form preparation from the polyester release film in production thereof was evaluated. Evaluation was performed in accordance with the following criteria.
4: Easily removable
3: Removable
2: Somehow removable
1: Somehow removable but torn
0: Not removable (2) Test on Disintegration in the Mouth The dissolution profile in the mouth was evaluated by the following test on disintegration in the mouth.

A 1000-mL glass petri dish was charged with 900 mL of a phosphate buffer solution (pH 6.8), and a stainless steel sieve (Φ mm) was submerged upside down in the solution. The solution was stirred (300 rpm) with a stirrer. The temperature of the solution was maintained at 37±2° C. using a constant-temperature water circulator. A test sample (3 cm$^2$) was put in the solution and a stainless steel net (aperture of 5 mm) having a size of 3 cm$^2$×3 cm$^2$ was placed thereon as a weight. The disintegration of the test sample was visually observed and the time required therefor from putting the test sample in the solution was measured with a stopwatch.

The above procedure was performed three times for test samples of each oral film-form preparation, and the average time was determined as the disintegration time in the mouth. The disintegration time in the mouth was converted into a score in accordance with the following criteria. The test sample which could not be removed in the releasability test (1) was evaluated to score 0.
4: 0 to 10 seconds
3: 10 to 15 seconds
2: 15 to 20 seconds
1: 20 seconds or longer (3) Tensile Strength Test and Bending Resistance Test The film strength was evaluated by the following tensile strength test and bending resistance test.

(3-1) Tensile Strength Test

A test sample cut to a size of 12 mm×50 mm was sufficiently dried in a desiccator and subjected to the tensile strength test using a small tabletop tensile tester (Shimadzu Corporation, EZ TEST-100M) in conformity with JIS K7127 "Plastics—Test conditions for films and sheets". The testing rate employed was 60 mm per minute. Since the test sample was hardly elongated, the tensile yield strength determined by the measurement was used as the tensile strength.

The test was performed three times for each test sample, and the average value was determined as the tensile strength. The tensile strength value was converted into a score in accordance with the following criteria. The test sample which could not be removed in the releasability test (1) was evaluated to score 0.
4: 10 to 20 N
3: 5 to 10 N
2: 2 to 5 N
1: 0 to 2 N (3-2) Bending Resistance Test The test was performed in conformity with "JIS L1096 general fabric test method 8.19 rigid flexible, 8.19.1 A method (45° cantilever method)".

Five pieces of test samples having a size of 20 mm×150 mm were prepared. The test sample was placed on a horizontal table having a 45° slope on one side and a smooth surface in such a manner that the short side of the test sample was aligned with the base line of the scale. Then, the test sample was slid slowly towards the slope by a suitable method, and when the central point of one end of the test sample comes in contact with the slope, the position of the other end was read using the scale.

The bending resistance is indicated by the moving distance (mm) of the test sample. Each test sample was inverted upside down and back and forth and measured for the bending resistance, and the average of the measured values was determined as the bending resistance. The evaluation criteria were set as follows on the basis of the bending resistance (about 60 mm) of the oral film-form preparation not containing any of amino acid, dipeptide, and nucleotide (Comparative Example 3) as the standard. The test sample which could not be removed in the releasability test (1) was evaluated to score 0.
4: Standard±10 mm
3: Standard±20 mm
2: Standard±30 mm
1: Standard±40 mm or more
(4) Test on Duration of Tackiness and Sensory Test (Tactile Impression)

The tactile impression when handled with fingers and the texture in the mouth were evaluated by the following test on duration of tackiness and sensory test (tactile impression).
(4-1) Test on Duration of Tackiness The test was performed using a rheometer (SUN SCIENTIFIC, CR-2000) in the environment illustrated in FIG. 2.

Figure 2:
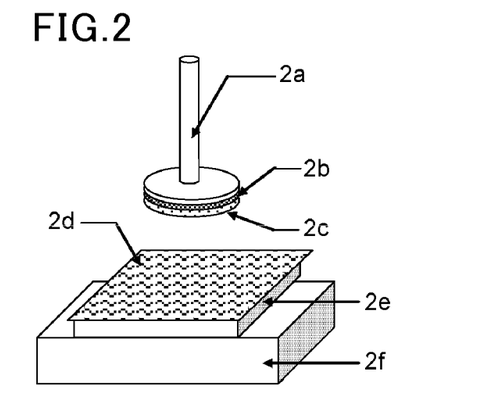
FIG. 2 is a schematic view illustrating a state of testing the duration of tackiness.

On probe $2a$ (Φ 12 mm), test sample $2c$ (Φ 12 mm) was attached by double-faced tape $2b$. Separately, rubber $2e$ was placed on test stand $2f$, and collagen film $2d$ soaked with water was placed thereon. An amount of 200 μL of purified water was added to the test sample $2c$. The probe $2a$ with the test sample $2c$ was moved downward to touch the collagen film $2d$ and then moved upward. At this time, the duration of tackiness after the initial tackiness that was observed when the probe $2a$ was removed from the collagen film $2d$ was measured using a caliper on the recording paper. The evaluation was performed based on the following criteria. The test sample which could not be removed in the releasability test (1) was cut together with the release film and attached to the probe by a double-faced tape with the release film side contacting the probe. The measurement was similarly performed.

4: 0 to 2 mm
3: 2 to 3 mm
2: 3 to 4 mm
1: 4 mm or more
(4-2) Sensory Test (Tactile Impression)

The oral film-form base was touched with fingers in a circular motion for 5 seconds, and the tactile impression (sticky or not) was observed. The evaluation was performed in accordance with the following criteria.
4: Not sticky
3: Sticky but not annoying
2: Uncomfortably sticky
1: Quite sticky and pieces of film were left on fingers
(5) Sensory Test (Taste)

The oral film-form preparation was kept in the mouth until the preparation was dissolved for evaluation of the influence on the taste. The evaluation was performed in accordance with the following criteria.
4: Favorable flavor
3: No/only slight bitter or unpleasant taste
2: Strong bitter or unpleasant taste
1: So strong bitter or unpleasant taste that does not allow holding the preparation in the mouth
(6) Usability Under Limitation in Carbohydrate Intake The usability of the oral film-form preparation under limitation in carbohydrate intake was evaluated based on the contained carbohydrate. The evaluation was performed in accordance with the following criteria.
4: Containing no carbohydrate
3: Containing tri- or higher saccharide
2: Containing disaccharide
1: Containing monosaccharide

TABLE 8

| Example | Releasability | Bending resistance | Tensile strength | Duration of tackiness | Disintegration in the mouth | Sense (tactile impression) | Sense (taste) | Usability under limitation in carbohydrate intake | Total |
|---|---|---|---|---|---|---|---|---|---|
| 1 | 4 | 4 | 4 | 4 | 4 | 4 | 4 | 4 | 32 |
| 2 | 4 | 3 | 3 | 4 | 4 | 4 | 4 | 4 | 30 |
| 3 | 4 | 3 | 4 | 4 | 3 | 4 | 4 | 4 | 30 |
| 4 | 4 | 4 | 4 | 3 | 4 | 3 | 4 | 4 | 30 |
| 5 | 4 | 4 | 4 | 4 | 4 | 4 | 3 | 4 | 31 |
| 6 | 4 | 3 | 4 | 4 | 4 | 4 | 3 | 4 | 30 |
| 7 | 4 | 4 | 4 | 3 | 4 | 4 | 3 | 4 | 30 |
| 8 | 4 | 4 | 4 | 4 | 4 | 3 | 3 | 4 | 30 |
| 9 | 4 | 4 | 3 | 4 | 3 | 4 | 4 | 4 | 30 |
| 10 | 4 | 3 | 4 | 4 | 4 | 3 | 4 | 4 | 30 |
| 11 | 4 | 4 | 2 | 4 | 4 | 4 | 4 | 4 | 30 |
| 12 | 4 | 4 | 3 | 4 | 3 | 4 | 4 | 4 | 30 |
| 13 | 4 | 4 | 3 | 4 | 4 | 4 | 4 | 4 | 31 |
| 14 | 4 | 4 | 2 | 4 | 4 | 4 | 4 | 4 | 30 |
| 15 | 4 | 4 | 3 | 4 | 4 | 4 | 4 | 4 | 31 |
| 16 | 4 | 4 | 3 | 4 | 4 | 4 | 4 | 4 | 31 |

TABLE 9

| Comparative Example | Releasability | Bending resistance | Tensile strength | Duration of tackiness | Disintegration in the mouth | Sense (tactile impression) | Sense (taste) | Usability under limitation in carbohydrate intake | Total |
|---|---|---|---|---|---|---|---|---|---|
| 1 | 2 | 1 | 1 | 2 | 2 | 2 | 4 | 4 | 18 |
| 2 | 4 | 2 | 3 | 2 | 3 | 2 | 4 | 4 | 24 |

TABLE 9-continued

| Comparative Example | Releasability | Bending resistance | Tensile strength | Duration of tackiness | Disintegration in the mouth | Sense (tactile impression) | Sense (taste) | Usability under limitation in carbohydrate intake | Total |
|---|---|---|---|---|---|---|---|---|---|
| 3 | 3 | 4 | 4 | 1 | 2 | 1 | 4 | 4 | 23 |
| 4 | 0 | 0 | 0 | 4 | 0 | 0 | 4 | 4 | 12 |
| 5 | 1 | 0 | 0 | 3 | 0 | 1 | 4 | 4 | 13 |
| 6 | 0 | 0 | 0 | 3 | 0 | 0 | 4 | 4 | 11 |
| 7 | 1 | 0 | 0 | 4 | 0 | 1 | 4 | 4 | 14 |
| 8 | 0 | 0 | 0 | 4 | 0 | 0 | 3 | 4 | 11 |
| 9 | 0 | 0 | 0 | 2 | 0 | 0 | 3 | 4 | 9 |
| 10 | 0 | 0 | 0 | 1 | 0 | 0 | 3 | 4 | 8 |
| 11 | 0 | 0 | 0 | 2 | 0 | 0 | 3 | 4 | 9 |
| 12 | 1 | 0 | 0 | 4 | 0 | 0 | 3 | 4 | 12 |
| 13 | 2 | 4 | 4 | 1 | 2 | 1 | 3 | 4 | 21 |
| 14 | 4 | 4 | 4 | 4 | 4 | 2 | 3 | 0 | 25 |
| 15 | 4 | 4 | 4 | 4 | 4 | 2 | 3 | 2 | 27 |
| 16 | 4 | 4 | 4 | 4 | 4 | 2 | 3 | 0 | 25 |
| 17 | 4 | 4 | 4 | 4 | 4 | 2 | 4 | 1 | 27 |
| 18 | 4 | 4 | 3 | 4 | 3 | 2 | 4 | 1 | 25 |
| 19 | 4 | 4 | 2 | 4 | 3 | 2 | 4 | 1 | 24 |
| 20 | 4 | 3 | 4 | 1 | 4 | 4 | 4 | 1 | 25 |
| 21 | 4 | 3 | 4 | 3 | 4 | 2 | 4 | 1 | 25 |
| 22 | 3 | 3 | 1 | 4 | 4 | 1 | 4 | 1 | 21 |

In Comparative Examples 1, 2, and 4 to 13, purified water was mainly used as a solvent in production of the oral film-form preparations, and therefore, the particles of amino acid, dipeptide, or nucleotide were unintendedly dissolved therein. As a result, the oral film-form preparations containing particles of amino acid, dipeptide, or nucleotide dispersed therein could not be obtained. Such oral film-form preparations could not have a rapid dissolution profile in the mouth or sufficient film strength, and the tactile impression when handled with fingers and the texture in the mouth were unfavorable (Table 8, 9).

To avoid these problems even in a case where the particles of amino acid, dipeptide, or nucleotide were dissolved, it may be considered to reduce the amount of the particles of amino acid, dipeptide, or nucleotide. In such a method, however, the amount of the edible polymer is relatively increased to possibly cause the similar problems.

INDUSTRIAL APPLICABILITY

The oral film-form base and the oral film-form preparation of the present invention have a rapid dissolution profile in the mouth and sufficient film strength, give a good tactile impression when handled with fingers and favorable texture and taste in the mouth. Moreover, in comparison with those containing sugar or sugar alcohol, the oral film-form base and the oral film-form preparation of the present invention containing particles of at least one compound selected from the group consisting of amino acid, dipeptide, and nucleotide prevent worsening of the tactile impression (sticky feeling) attendant on moisture absorption by a saccharide and are administrable to those who have limitation in carbohydrate intake.

In production of the oral film-form base and the oral film-form preparation of the present invention, the particles of at least one compound selected from the group consisting of amino acid, dipeptide, and nucleotide do not need to be preliminarily dissolved in the solution but can be dispersed or supported in the state of particles. Accordingly, the oral film-form base and the oral film-form preparation of the present invention can be efficiently produced, and the particle size and the particle form can be controlled.

REFERENCE SIGNS LIST

1a. Particles of at least one compound selected from the group consisting of amino acid, dipeptide, and nucleotide
1b. Edible film
2a. Probe
2b. Double-faced tape
2c. Test sample
2d. Collagen film
2e. Rubber
2f. Test stand

The invention claimed is:

1. An oral film-form base comprising
an edible polymer soluble in water and an organic solvent having a solubility parameter of 9.7 or higher, and
particles of at least one compound selected from the group consisting of amino acid, dipeptide, and nucleotide,
the particles of at least one compound selected from the group consisting of amino acid, dipeptide, and nucleotide being dispersed in the state of particles in the oral film-form base,
wherein the oral film-form base does not contain sugar or sugar alcohol.

2. The oral film-form base according to claim 1, wherein the particles of at least one compound selected from the group consisting of amino acid, dipeptide, and nucleotide have an average particle size of 0.1 to 60 μm.

3. The oral film-form base according to claim 1, wherein the edible polymer soluble in water and an organic solvent having a solubility parameter of 9.7 or higher is solid at ambient temperature.

4. The oral film-form base according to claim 3, wherein the edible polymer soluble in water and an organic solvent having a solubility parameter of 9.7 or higher is at least one of polyvinyl pyrrolidone and hydroxypropyl cellulose.

5. The oral film-form base according to claim 4, wherein the polyvinyl pyrrolidone has a weight average molecular weight of 2500 to 3000000.

6. The oral film-form base according to claim 4, wherein the hydroxypropyl cellulose has a weight average molecular weight of 10000 to 1150000.

7. The oral film-form base according to claim 4, wherein the hydroxypropyl cellulose has a hydroxypropoxyl substitution degree of 50 to 100%.

8. The oral film-form base according to claim 1, produced using an organic solvent having a solubility parameter of 9.7 or higher.

9. An oral film-form preparation comprising the oral film-form base according to claim 1 and a drug dispersed or dissolved in the oral film-form base.

* * * * *